(12) United States Patent
Kamiyama

(10) Patent No.: US 7,713,208 B2
(45) Date of Patent: May 11, 2010

(54) ULTRASOUND DIAGNOSTIC APPARATUS

(75) Inventor: Naohisa Kamiyama, Otawara (JP)

(73) Assignee: Kabushiki Kaisha Toshiba, Kawasaki-shi (JP)

( * ) Notice: Subject to any disclaimer, the term of this patent is extended or adjusted under 35 U.S.C. 154(b) by 1297 days.

(21) Appl. No.: 11/071,294

(22) Filed: Mar. 4, 2005

(65) Prior Publication Data

US 2005/0154305 A1    Jul. 14, 2005

Related U.S. Application Data

(62) Division of application No. 09/696,965, filed on Oct. 27, 2000, now Pat. No. 6,918,876.

(30) Foreign Application Priority Data

Oct. 29, 1999 (JP) ................................ 11-309381

(51) Int. Cl.
*A61B 8/14* (2006.01)
(52) U.S. Cl. ...................... 600/458; 600/437
(58) Field of Classification Search ................ 600/437, 600/439, 444, 446, 458; 601/2–4; 604/20–24
See application file for complete search history.

(56) References Cited

U.S. PATENT DOCUMENTS

| | | | |
|---|---|---|---|
| 4,694,434 A | 9/1987 | von Ramm et al. | |
| 4,993,417 A | 2/1991 | Seo | |
| 5,285,788 A | 2/1994 | Arenson et al. | |
| 5,438,994 A | 8/1995 | Starosta et al. | |
| 5,462,057 A | 10/1995 | Hunt et al. | |
| 5,568,812 A * | 10/1996 | Murashita et al. | 600/440 |
| RE35,371 E | 11/1996 | Seo | |
| 5,617,863 A | 4/1997 | Roundhill et al. | |
| 5,694,937 A * | 12/1997 | Kamiyama | 600/443 |
| 5,833,613 A | 11/1998 | Averkious et al. | |
| 5,908,390 A | 6/1999 | Matsushima | |
| 5,971,928 A * | 10/1999 | Dodd et al. | 600/458 |
| 5,980,458 A * | 11/1999 | Clark | 600/437 |
| 6,066,099 A | 5/2000 | Thomenius et al. | |
| 6,193,663 B1 | 2/2001 | Napolitano et al. | |
| 6,315,729 B1 | 11/2001 | Averkiou et al. | |

OTHER PUBLICATIONS

P. Dayton, K. Morgan, M. Allietta, A. Klibanov, G. Brandenburger, and K. Ferrara, Simultaneous Optical an Acoustical Observations and Contrast Agents, IEEE Ultrasonics Symposium, 1997, p. 1583-1591.

* cited by examiner

*Primary Examiner*—Long V Le
*Assistant Examiner*—Saurel J Selkin
(74) *Attorney, Agent, or Firm*—Oblon, Spivak, McClelland, Maier & Neustadt, L.L.P.

(57) ABSTRACT

An ultrasound diagnostic apparatus for obtaining an ultrasound image of a subject into which an ultrasound contrast agent mainly composed of microbubbles is injected, comprising a probe configured to transmit/receive an ultrasound wave to/from the subject, a transmission circuit configured to drive the probe to transmit an ultrasound wave while sequentially changing a direction of an ultrasound transmission line, a reception circuit configured to generate reception line data of the number of parallel reception from ultrasound echo signals obtained by one ultrasound wave transmission, a transmission/reception control circuit configured to control the transmission and reception circuits to change the number of parallel reception during a scan sequence for generating a 1-frame ultrasound image, and an image processing unit configured to generate an ultrasound image on the basis of the reception line data.

3 Claims, 11 Drawing Sheets

FIRST TRIGGER

SECOND TRIGGER

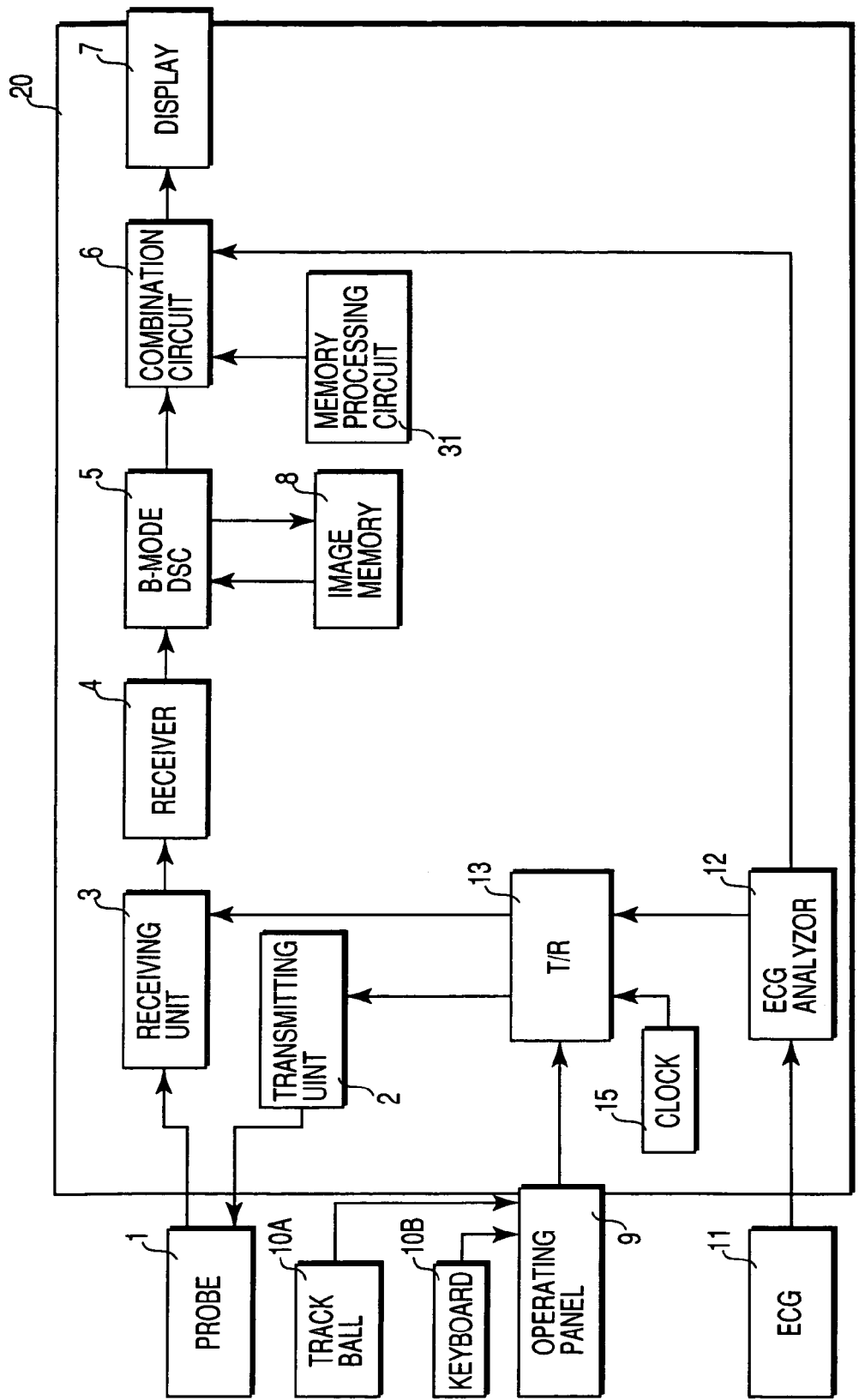
F I G. 18

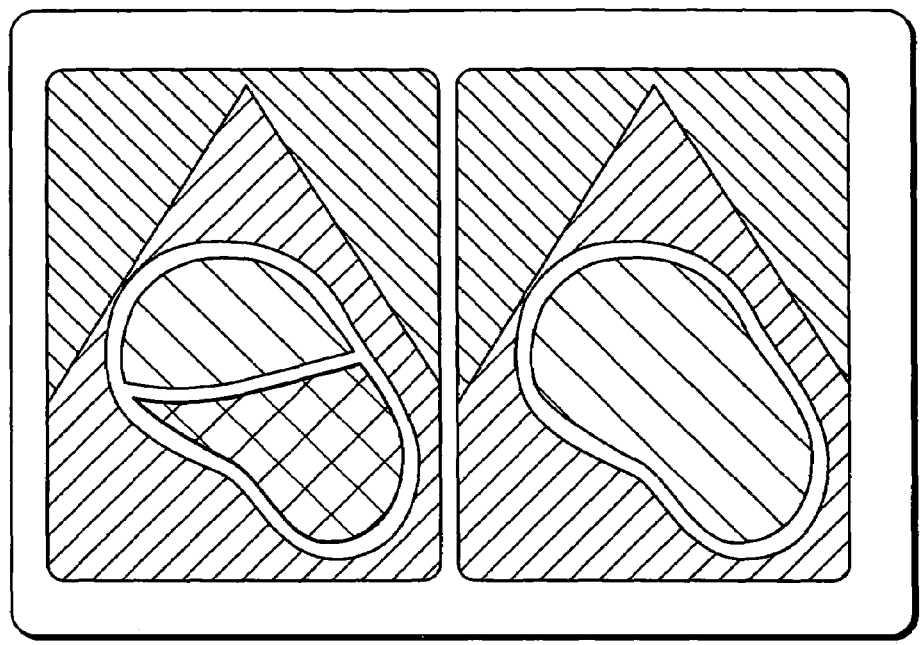
REAL TIME IMAGE   COMBINED IMAGE
F I G. 21A
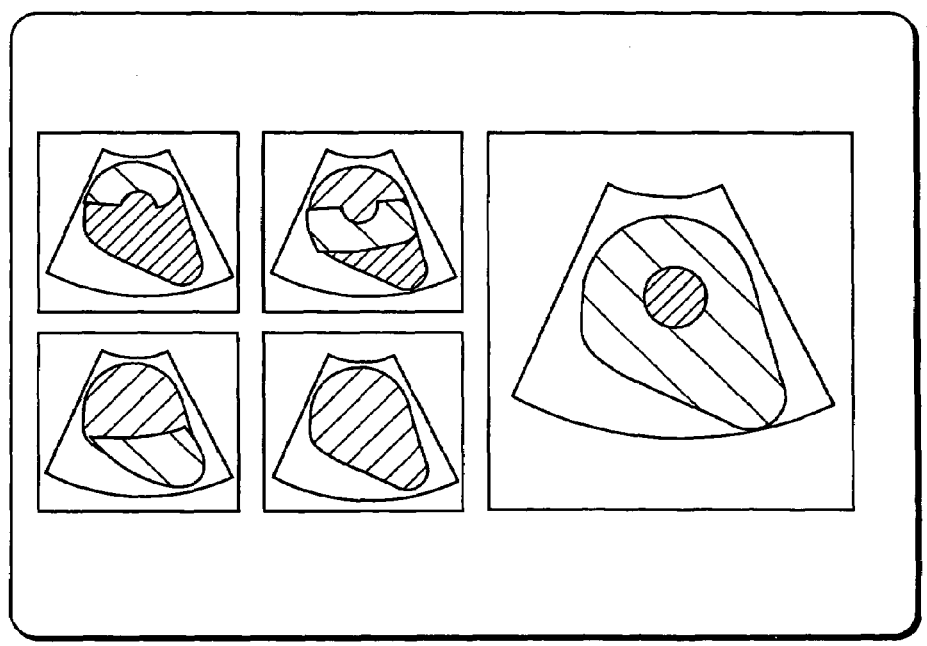
TRIGGER IMAGES   COMBINED IMAGE
F I G. 21B

ULTRASOUND DIAGNOSTIC APPARATUS

This application is a division of and claims priority to U.S. patent application Ser. No. 09/696,965 filed Oct. 27, 2000. The entire contents of this application are incorporated herein by reference.

CROSS-REFERENCE TO RELATED APPLICATIONS

This application is based upon and claims the benefit of priority from the prior Japanese Patent Application No. 11-309381, filed Oct. 29, 1999, the entire contents of which are incorporated herein by reference.

BACKGROUND OF THE INVENTION

The present invention relates to an ultrasound diagnostic apparatus suited for a contrast echo method using an ultrasound contrast agent mainly composed of microbubbles.

An ultrasound image diagnostic apparatus has many advantages which other modalities, e.g., an X-ray diagnostic apparatus, X-ray computer tomography apparatus (CT scanner), magnetic resonance imaging apparatus (MRI), and nuclear medicine diagnostic apparatus (gamma camera, SPECT, and PET), do not have. For example, the ultrasound image diagnostic apparatus can generate and display images almost in real time concurrently with scanning. This apparatus is compact and inexpensive. In using the apparatus, there is no chance of exposure to radiation. The apparatus can easily visualize blood flow.

(Contrast Agent)

Ultrasound contrast media are now being put into practice, and an improvement in the precision of vascularity examination using such a contrast agent is expected. A contrast agent mainly consists of microbubbles of several microns. Microbubbles rapidly shrink and collapse upon reception of strong ultrasound waves. The contrast enhance effect therefore lasts only for a relatively short period of time.

In actual scan operation, since fresh contrast agent is continuously supplied to a scan slice over a blood flow, a certain degree of contrast enhance effect may be maintained. In general, however, ultrasound waves are applied several thousand times per second. In organs in which the blood flow rate is low or a relatively thin blood vessel, a contrast enhance effect can be maintained only for a moment.

(Intermittent Transmission Method)

That a contrast agent instantaneously collapses upon application of ultrasound waves is the most serious problem in the contrast echo method. As a technique of solving this problem, an intermittent transmission method is available. In this technique, scanning is intermittently repeated in synchronism with the R waves in an electrocardiogram. Fresh contrast agent continuously flows into a slice in the intervals between scans. This ensures a contrast enhance effect for every scan.

(Harmonic Imaging)

The utility of the above contrast echo method is augmented if it is used in combination with a harmonic imaging method. Microbubbles vibrate nonlinearly when ultrasound waves collide with them. This nonlinear vibrations produce harmonic components having frequencies of integer multiples of a fundamental frequency. Harmonic imaging is an imaging technique of extracting harmonic components from a fundament frequency component and visualizing them. Organs hardly vibrate nonlinearly, and hence harmonic components from the organs is pelatively small. Consequently, a region where a contrast agent exists is relatively emphasized.

As described above, if the intermittent transmission method is used, since fresh microbubbles flow into a slice during scan intervals, a contrast enhance effect can be maintained. On the other hand, in order to ensure a certain spatial resolution, about 100 to 200 ultrasound scanning lines are required per frame. That is, ultrasound pulses are applied at least a number of times equal to the number of ultrasound scanning lines in one scan.

In scanning, ultrasound pulses are transmitted while their directions are gradually changed. Therefore, microbubbles on a scanning line adjacent to a scanning line having undergone transmission/reception may not collapse. In practice, however, since an ultrasound beam has a certain width, most microbubbles on the adjacent scanning line collapse in many cases.

In addition, the width of an ultrasound beam changes in accordance with depth. The contrast enhance effect therefore may change depending on depth. Specific problems will be described below with reference to FIGS. 1A and 1B.

When ultrasound pulses are generated from a plurality of arrayed transducers 51 while the generation timing is gradually shifted, a convergent sound field is formed. The depth of ultrasound focus point can be arbitrarily changed by changing the timing. Referring to FIG. 1A, when a focus point is formed on a scanning line with an arrow 52 at a relatively short distance, a region exhibiting a relatively high pressure sound, i.e., a region 53 exhibiting a relatively high degree of microbubble collapse (microbubble collapse region), is indicated by the hatching. The dotted lines represent adjacent ultrasound scanning lines 54.

As shown in FIG. 1A, a short-distance focus point is often formed by driving only transducers near the center instead of driving all the transducers 51. In this case, in the short-distance region, the ultrasound beam is narrow, and hence the microbubble collapse range 53 is also narrow. In the long-distance region, the ultrasound beam is relatively wide, but the ultrasound scanning line pitch is also large. In addition, ultrasound waves greatly attenuate because of the long propagation distance. As a result, the microbubble collapse range 53 becomes relatively narrow.

FIG. 1B shows a microbubble collapse range 55 when a focus point is formed at a relatively long distance. As shown in FIG. 1B, to ensure a certain degree of sound pressure at the focus point even at a long distance with a long propagation distance, many transducers must be driven at a high voltage. In this case, in the short-distance region, the ultrasound beam becomes wide and the microbubble collapse range 55 also becomes relatively wide. As a consequence, microbubbles on adjacent ultrasound scanning lines collapse. When, therefore, ultrasound transmission/reception is performed afterward in this scanning line direction, microbubbles will have collapsed and been lost.

Another problem will be described next. Consider a case wherein a cardiac minor axis image is obtained by the contrast echo method. As shown in FIG. 2, if a focus point is set at a short distance in accordance with a depth 61 of a cardiac muscle front wall portion 61, a rear wall portion 62 is hardly visualized due to biological damping and a curtain effect due to microbubbles filling a cardiac cavity.

If a focus point is set at a long distance in accordance with the rear wall portion 62, applied ultrasound pulses collapse microbubbles on adjacent ultrasound scanning lines in the short-distance region. Therefore, no contrast enhance effect can be expected at the front wall portion 61.

It is known that in the sector scan method, when ultrasound waves are transmitted in a direction greatly shifted from a direction perpendicular to the probe vibration surface, a decrease in sound pressure and an increase in side lobe level occur as compared with application of ultrasound wave in the direction perpendicular to the problem vibration surface. That is, when ultrasound waves are applied to a cardiac muscle side wall portion 63, side lobes collapse microbubbles near the front wall portion 61 and rear wall portion 62.

It follows from the above description that it is practically impossible to transmit ultrasound waves so as to form a uniform sound field distribution on an entire scan slice. The luminance reference level is therefore not uniform within the scan slice and varies. Since scattering by tissue exhibits a relatively linear response, luminance can theoretically be made uniform by level correction for reception signals. However, a response of microbubbles exhibits strong nonlinearity, and phenomena such as nonlinear vibrations, expansion, and collapse of microbubbles, vary in a complicated manner depending on the absolute level of applied sound pressure. Therefore, it is practically impossible to correct reception signals.

BRIEF SUMMARY OF THE INVENTION

It is an object of the present invention to allow an ultrasound diagnostic apparatus to exhibit a contrast enhance effect based on an ultrasound contrast agent within a slice as uniformly as possible.

An ultrasound diagnostic apparatus according to the present invention comprises an ultrasound diagnostic apparatus for obtaining an ultrasound image of a subject into which an ultrasound contrast agent mainly composed of microbubbles is injected, comprising: a probe configured to transmit/receive an ultrasound wave to/from the subject; a transmission circuit configured to drive the probe to transmit an ultrasound wave while sequentially changing a direction of an ultrasound transmission line; a reception circuit configured to generate reception line data of the number of parallel reception from ultrasound echo signals obtained by one ultrasound wave transmission; a transmission/reception control circuit configured to control the transmission and reception circuits to change the number of parallel reception during a scan sequence for generating a 1-frame ultrasound image; and an image processing unit configured to generate an ultrasound image on the basis of the reception line data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 18 is a block diagram showing an ultrasound diagnostic apparatus according to the third embodiment of the present invention;

FIGS. 21A and 21B are views showing display examples in the third embodiment.

DETAILED DESCRIPTION OF THE INVENTION

The preferred embodiments of the present invention will be described in detail below with reference to the views of the accompanying drawing. Consider a clinical case wherein an anomalous region is identified by diagnosing the flow of blood into the liver parenchyma or cardiac muscle by the contrast echo method.

First Embodiment

Arrangement and Flow of Signals

Figure 3:
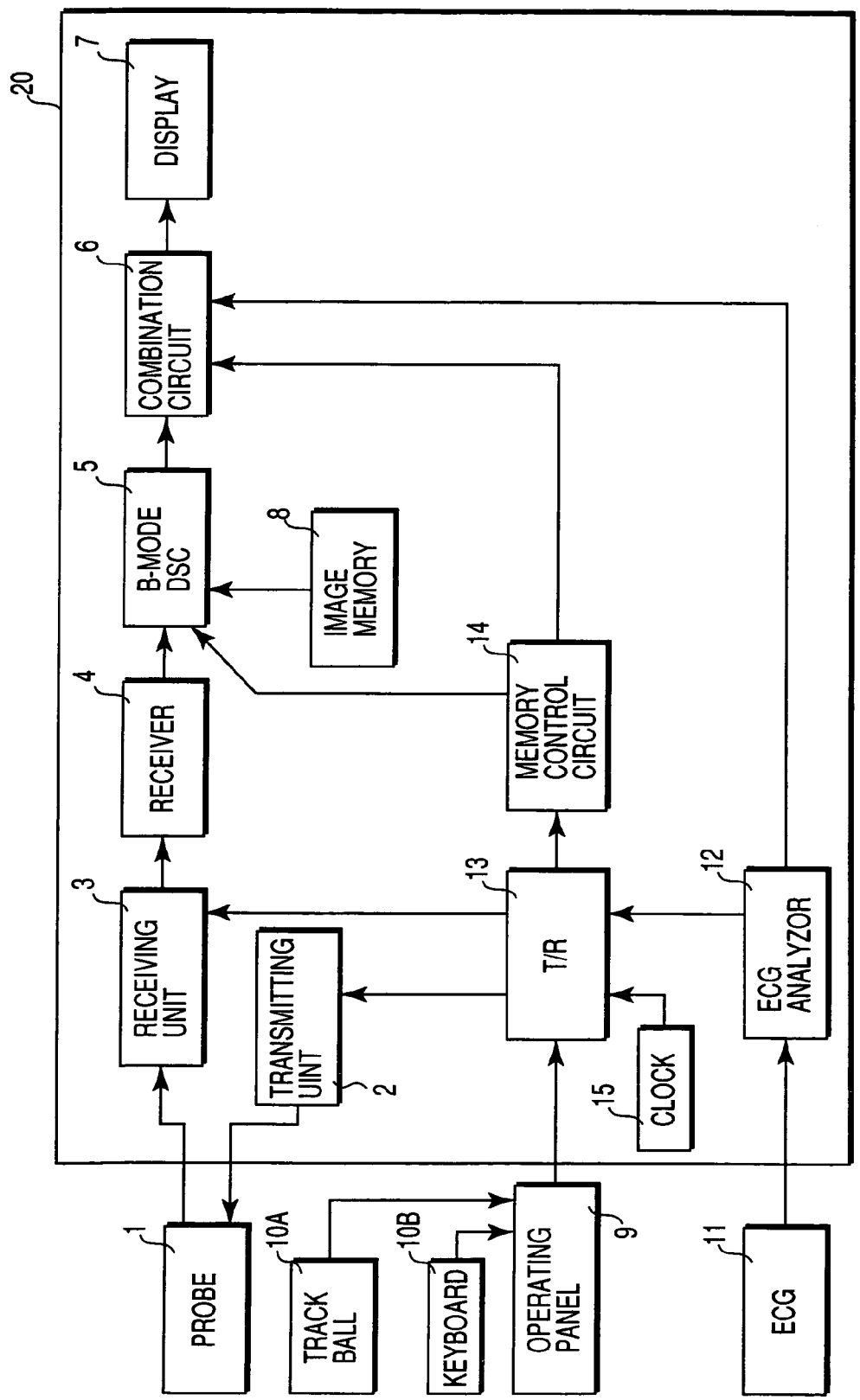
FIG. 3 is a block diagram showing the arrangement of an ultrasound diagnostic apparatus according to the first embodiment of the present invention.

FIG. 3 shows the arrangement of an ultrasound diagnostic apparatus according to the first embodiment. An ultrasound probe 1 is connected to an apparatus body 20. The apparatus body 20 scans the inside of an object to be examined by using an ultrasound beam through the ultrasound probe 1, creates tomographic image data by processing the obtained reception signal, and displays the image. An operating panel 9 having a trackball 10A, keyboard 10B, and the like is connected to the apparatus body 20. Various operator instructions such as an instruction to set a region of interest (ROI) are input to the apparatus body 20 through the operating panel 9.

A plurality of electroacoustic conversion elements (transducers) are arrayed on the distal end portion of the ultrasound probe 1. One or a few adjacent transducers constitute one channel. RF voltage pulses are applied from a transmitting unit 2 of the apparatus body 20 to the transducers. The transducers convert the electrical vibrations of the RF voltage pulse into mechanical vibrations. With this operation, the transducers generate ultrasound waves. Time differences in the application timing of high-frequency voltage pulses are provided between channels. These time differences, delay times in general, are set such that ultrasound waves generated by the transducers are combined into one narrow beam, and the beam is deflected as needed. By changing the delay times, the focal length and deflection angle can be arbitrarily changed. A transmission/reception control circuit (T/R) 13 controls these delay times.

Ultrasound waves propagate through the object and are reflected by an acoustic-impedance discontinuous surface located at some point in the object. The reflected waves return as echoes to the probe 1. The echoes mechanically vibrate the transducers of the probe 1. As a consequence, weak current signals are generated. A receiving unit 3 amplifies the current signals in units of channels, converts them into voltage signals, and converts them into digital signals. In addition, the receiving unit 3 adds the signals while giving them delay times that differ between the channels. This addition is processing called digital beam forming, by which a reception signal is given a directivity. The receiving unit 3 has a plurality of digital beam forming systems. The transmission/reception control circuit (T/R) 13 simultaneously generates a plurality of reception signals having different directivities by parallel processing and differently controlling delay times between the digital beam forming systems.

The transmission/reception control circuit 13 implements scan operation (to be described later) according to the present invention by controlling delay times in transmission and reception. Note that scan operation is defined as operation to acquire a plurality of reception signals required for the creation of a 1-frame image. More specifically, scan operation is operation of repeating a series of ultrasound beam transmitting/receiving operations with respect to a plurality of ultrasound scanning lines constituting a scan plane. This new scan sequence makes it possible to obtain both the effect of improving the time resolution and the effect of making the contrast enhance effect of microbubbles relatively uniform within a scan plane.

In addition to the transmission/reception delay control function, the transmission/reception control circuit 13 has basic control functions such as the function of setting a transmission frequency and the function of shaping the waveform of a transmission pulse. As described above, by changing the delay times in transmission/reception, the transmission direction, reception direction, focal length, and ultrasound scanning line density of ultrasound beams can be arbitrarily changed. In general, parameters such as delay time and transmission frequency differ between modes such as the B-mode and color Doppler mode. B-mode and color mode data can be simultaneously obtained by alternately transmitting these waves.

A receiver 4 and subsequent components will be described next. The receiver 4 is comprised of a logarithmic amplifier, an envelope detection circuit, a band-pass filter for extracting harmonic components from a reception signal, and the like.

An output from the receiver 4 is converted by a B-mode DSC 5 from a fan array of ultrasound scanning lines into an orthogonal array of scanning lines corresponding to a standard video format. The resultant data is sent as a bit stream to a combination circuit 6. The combination circuit 6 combines image data and additional information such as an electrocardiographic waveform and various set values into one frame, thereby forming a frame to be finally displayed on a display 7.

A memory control circuit 14 sends array conversion information to the B-mode DSC 5 and combination circuit 6.

An image memory 8 temporarily stores the signal train after the array conversion by the B-mode DSC 5 (or the signal train before the array conversion). This information is read out by an operator after a diagnosis or the like. In this case, the information is output to the display 7 through the B-mode DSC 5 and combination circuit 6.

An ECG analyzer 12 analyzes the electrocardiograph (ECG) data of the object measured by an ECG 11, extracts, for example, R waves, and generates a trigger signal to the transmission/reception control circuit 13. The ECG analyzer 12 converts the electrocardiograph data into display data and sends it to the combination circuit 6. This electrocardiograph data and tomographic image data are combined into a single frame to be displayed together on the display 7. A clock 15 is used to control intermittent transmission intervals in a diagnosis using on ECG signal, e.g., a diagnosis of an abdominal organ. Note that the operator can control the intermittent transmission intervals and timing on the operating panel, and the control operation is reflected in the transmission/reception control circuit 13.

(Scan Operation)

Figure 4:
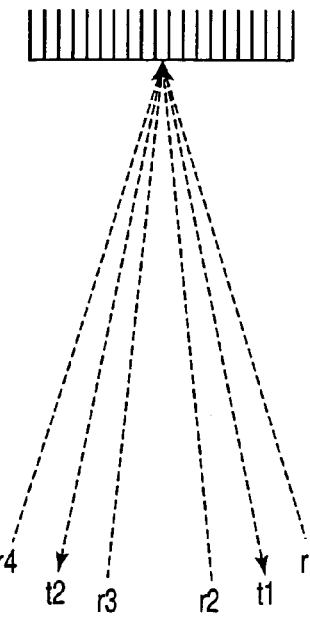
FIG. 4 is a view for explaining parallel signal processing used in scan operation in the first embodiment.

The scan operation in this embodiment will be briefly described by exemplifying the parallel signal processing of simultaneously generating a plurality of reception signals having different directivities for one transmitting operation. Consider a case wherein two reception signals having different directivities are obtained for one scanning operation. FIG. 4 is a view for explaining the principle of parallel signal processing. Referring to FIG. 4, "r" represents an ultrasound scanning line; and "t", the transmission direction. Ultrasound pulses are transmitted under delay control corresponding to the direction of an ultrasound scanning line t1. From the resultant echo signals, digital beam formers of two systems generate two types of reception signals that are given directivities in the directions of ultrasound scanning lines r1 and r2 under two types of delay control. A reception scanning line density twice a transmission scanning line density is realized by this parallel signal processing. Obviously, four or more reception signals with different directivities can be theoretically generated for one transmitting operation.

The scan operation in this embodiment will be described in detail next with reference to FIGS. 5A and 5B. Assume that one scan plane consists of 160 ultrasound scanning-lines. The angle difference between adjacent ultrasound scanning lines is represented by $\theta$.

Scan operation for acquiring reception signals required to generate a 1-frame image is constituted by a plurality of, two in this case, partial scan operations. More specifically, in the first partial scan operation, the first portion in the scan region is scanned, and in the second partial scan operation, the remaining, second portion in the scan region is scanned. A partial image of the first portion obtained by the first partial scan operation and a partial image of the second portion obtained by the second partial scan operation are combined into one frame, thereby completing a 1-frame image of the entire scan plane.

In the first and second partial scan operations, the focus point is fixed to a long distance. FIG. 5A shows the first partial scan operation. FIG. 5B shows the second partial operation. As shown in FIG. 5A, ultrasound transmission/reception is repeated in predetermined cycles. A transmission beam is sequentially moved from the right end to the left end of a scan plane in each transmission/reception. The intervals at which a transmission beam is moved are set to an integer multiple equal to or more than two of the angle difference θ between ultrasound scanning lines, 4·θ in this case.

In digital beam forming, a plurality of, four in this case, reception signals having different directivities are generated in every transmission by parallel signal processing. More specifically, four reception signals having directivities corresponding to fourth ultrasound scanning lines which are symmetrical about a transmission beam are generated.

These four reception signals are subjected to detection and luminance conversion in the receiver 4 and written in the B-mode DSC 5. Different write sequences for these signals are used in a short-distance region A and long-distance region B. In the short-distance region A, all the four reception signals are written. In the long-distance region B, only the two reception signal corresponding to the two ultrasound scanning line located in the center are written.

Figure 1A:
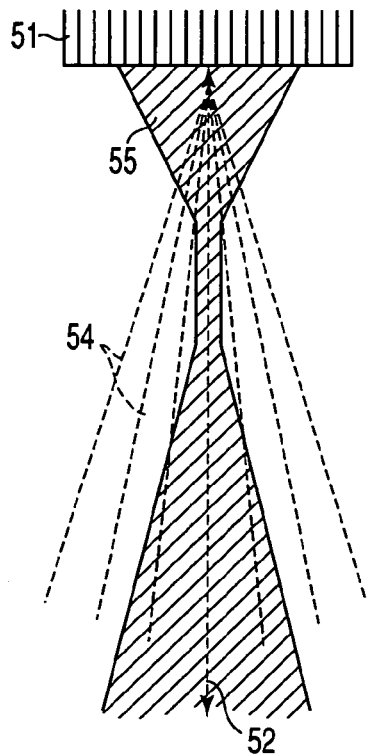
FIG. 1A is a view showing a microbubble collapse range when a focus point is formed at a relatively short distance in the prior art.
Figure 1B:
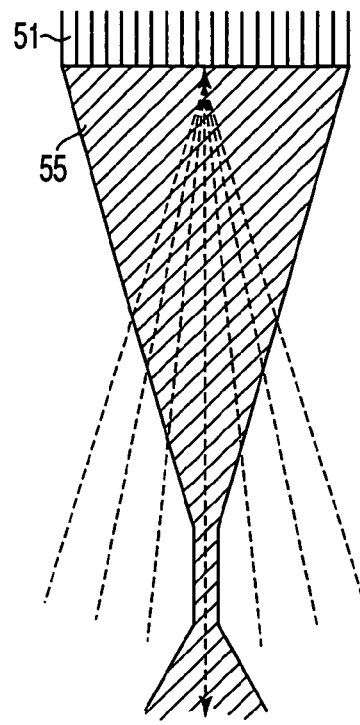
FIG. 1B is a view showing a microbubble collapse range when a focus point is formed at a relatively long distance.
Figure 2:
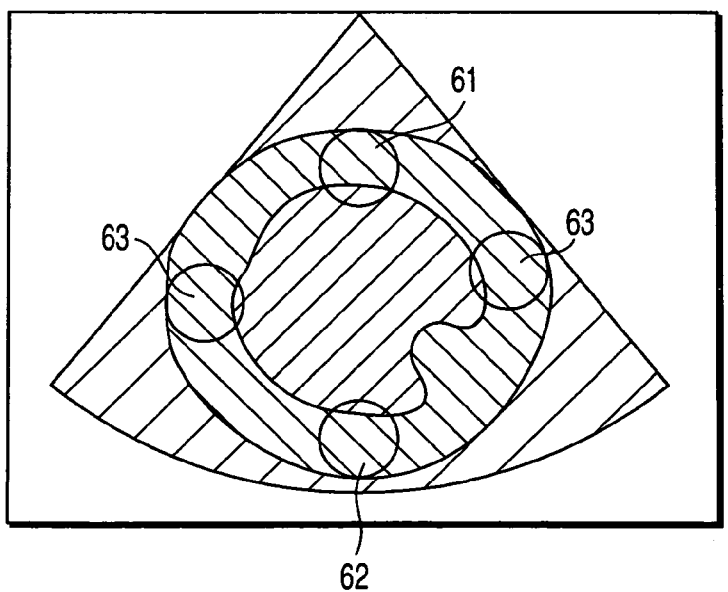
FIG. 2 is a view for additionally explaining problems in the prior art.
Figure 6:
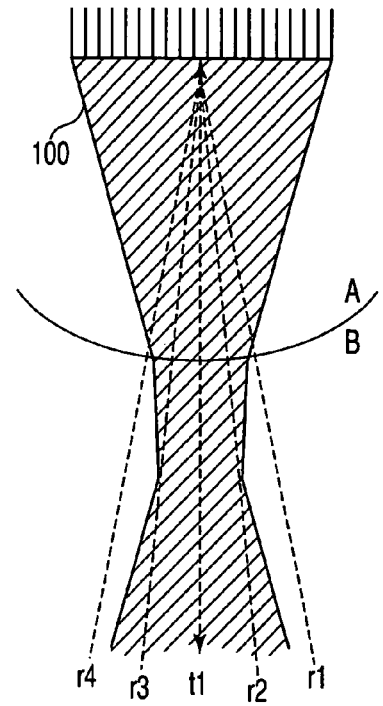
FIG. 6 is a view showing the details of FIG. 5A.

This first partial scan operation will be described in detail below with reference to FIG. 6. FIG. 6 shows a microbubble collapse range 100 in which a high contrast enhance effect is obtained when the focus point is formed at a relatively long distance. The long-distance focal point is formed under a typical transmission condition, i.e., a wide aperture and high driving voltage. In this condition, the width of the microbubble collapse range 100 is wide at the short-distance region A and narrow at the long-distance region B, as described with reference to FIG. 1B. The contrast enhance effect is high within the microbubble collapse range 100.

In accordance with this region exhibiting a high contrast enhance effect, in the short-distance region A, all four reception signals (luminance signals) corresponding to four ultrasound scanning lines r1, r2, r3, and r4 which are symmetrical about a transmission beam t11 are written in the B-mode DSC 5. In the long-distance region B, only the two reception signal corresponding to the two ultrasound scanning lines located in the center are written in the B-mode DSC 5.

The transmission beam is them moved to t12, and all four reception signals (luminance signals) corresponding to four ultrasound scanning lines r5, r6, r7, and r8 which are symmetrical about the transmission beam t12 are written in the B-mode DSC 5. In the long-distance region B, only the two reception signals corresponding to the two ultrasound scanning lines located in the center are written in the B-mode DSC 5.

When the first partial scan operation is completed upon repeating this sequence, on the memory of the B-mode DSC 5, the entire short-distance region A is filled with the luminance data, and the long-distance region B partially has luminance data blank portions. These blank portions are filled with the luminance data obtained by the second partial scan operation.

Disregarding averaging, the number of times of transmission/reception required for the first partial scan operation is 160/4=40.

As is obvious, since only the reception signals within the microbubble collapse range 100 need be finally used for an image, unnecessary reception signals need not be generated in the first partial scan operation, i.e., the reception signals corresponding to the two outside ultrasound scanning lines in the long-distance region B need not be generated by digital beam forming.

The second partial scan operation will be described next. In the first partial scan operation, data blank portions are present at two adjacent ultrasound scanning lines in the long-distance region B. Referring to FIG. 5A, for example, ultrasound scanning lines r4 and r5 correspond to blank portions. In the second partial scan operation, transmission, digital beam forming, and DSC write operation are performed to fill these blanks with data, as shown in FIG. 5B.

Ultrasound transmission/reception is repeated in predetermined cycles like the first partial scan operation. A transmission beam is sequentially moved from the right end to the left end of a scan plane in every transmitting/receiving operation. The intervals at which the transmission beam is moved are set to 4·θ as in the first partial scan operation. However, the transmission beam in the second partial scan operation is shifted from the transmission beam in the first partial scan operation by half the moving intervals of the transmission beam, i.e., 2·θ. With this operation, an ultrasound beam is transmitted in the direction of the center axis of each ultrasound scanning line corresponding to a blank portion formed in the first partial scan operation. The first transmission beam in the second partial scan operation is transmitted to a direction t21 between blank scanning lines r4 and r5. The next transmission beam is transmitted in a direction t22 between blank scanning lines r8 and r9. In this manner, transmission is repeated at intervals of 4·θ.

In digital beam forming, a plurality of, two in this case, reception signals having different directivities are generated by parallel signal processing for each transmitting operation. More specifically, two reception signals having directivities corresponding to left and right ultrasound scanning lines on the two sides of a transmission beam are generated.

These two reception signals are subjected to detection and luminance conversion in the receiver 4, and only the data corresponding to the data blank portions in the long-distance region B formed in the first partial scan operation are written in the B-mode DSC 5.

Figure 5A:
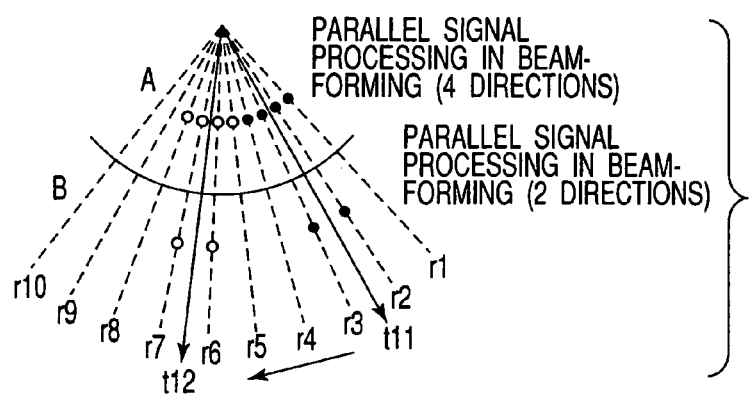
FIG. 5A is a view for explaining the first partial scan operation in the first embodiment.
Figure 5B:
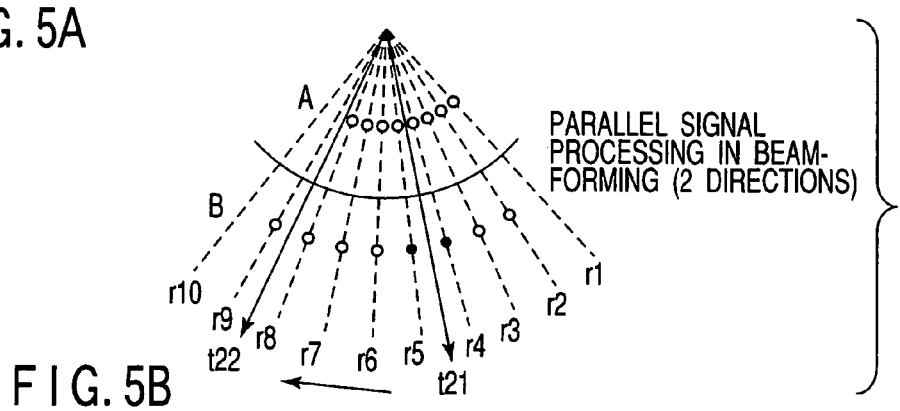
FIG. 5B is a view for explaining the second partial scan operation in the second embodiment.

As described above, in the second partial scan operation, image portions are assembled such that they do not overlap the image portions generated in the first partial scan operation in FIG. 5A, and no blank portions are formed. The number of times of transmission/reception in FIG. 5B is set to 40 (39, to be exact) as in the case shown in FIG. 5A. That is, transmission/reception is performed a total of 80 times, which is equal to the number of times of transmission/reception in 2-direction parallel signal processing. That is, the frame rate does not decrease.

The merits of this scan operation will be described below. At a long-distance focus point, the beam width increases in the short-distance region A. In this short-distance region A, microbubbles collapse in a wide range. In other words, in the short-distance region A, a contrast enhance effect owing to microbubbles can be obtained in a wide range. This makes it possible to effectively generate reception signals at once from a wide range corresponding to as many as four scanning lines for one transmitting operation by 4-direction parallel signal processing. On the other hand, in the long-distance region B, the intervals between ultrasound scanning lines become larger than those between ultrasound scanning lines in the short-distance region A, and the distance from the center of a transmission beam increases, resulting in a decrease in the intensity of ultrasound waves. If 4-direction parallel signal processing is performed in this state, sensitivity deteriorates. For this reason, in the first partial scan operation, 2-direction parallel signal processing is performed. In the second partial scan operation, then, only the blank regions in the first partial scan operation are filled with data. That is, the blank regions in the first partial scan operation correspond to data on scanning line pairs in the long-distance region. At a long-distance focus point, the scanning lines in these blank regions are included in the microbubble collapse range exhibiting a high contrast enhance effect. In this manner, high contrast enhance effects can be ensured in both the long- and short-distance regions.

In this case, for the sake of simplicity, the short-distance region A and long-distance region B are separated from each other by a clear boundary. To obtain a smoother image, these regions may overlap. In this case, for example, the luminance image on the overlapping portion is averaged to make the boundary less noticeable.

This scan operation is especially effective for sector scan operation in which ultrasound scanning line intervals differ in a short-distance region and long-distance region. However, effects similar to those described above can also be obtained when this operation is applied to linear scan operation in which ultrasound scanning line intervals remain unchanged in a short-distance region and long-distance region.

In addition, this technique may be used in combination with the intermittent transmission method of performing transmission in synchronism with an ECG signal. In this case, since the application of ultrasound waves is stopped during periods other than synchronous periods, more microbubbles flow into a slice of a region of interest and are stored without collapse. Obviously, if ultrasound waves are applied in this state, more microbubbles can be detected. In addition, if the scanning method of this embodiment is used, the contrast enhance effect can be relatively improved.

(Other Examples of Scanning Method)

Figure 7A:
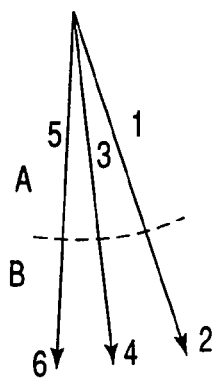
FIG. 7A is a view for explaining a multifocus method used in another partial scan operation in the first embodiment.

A multifocus method is available as a conventional method similar to the scanning method to be described below. The multifocus method is currently implemented in many apparatuses. This method will be described first with reference to FIGS. 7A and 7B. According to the multifocus method, as shown in FIG. 7A, (a) the respective ultrasound scanning lines are scanned to perform transmission/reception at a short-distance focus point so as to generate a signal component corresponding to a short-distance region A, and (b) a signal component corresponding to a long-distance region B is generated at a long-distance focus point. These two images are then combined into a 1-frame tomographic image. Each ultrasound scanning line has two focus points (represented by the heads of the arrows in FIG. 7A), and hence the resolution increases. However, since the number of times of transmission/reception increases twice, the frame rate decreases to half. In addition, a multifocus method using three or more focus points is also available.

In the above method, if the position of the focus point is sequentially changed from the short-distance region, microbubble echoes may be detected up to a deep portion while microbubbles collapse from the short-distance region. However, microbubbles on adjacent ultrasounds collapse.

Figure 7B:
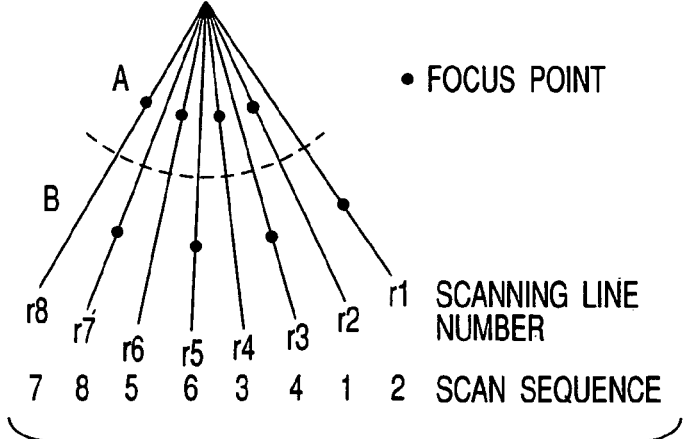
FIG. 7B is a view for explaining the partial scan operation in the first embodiment which uses the multifocus method in FIG. 7B.

The second example of the scanning method of this embodiment, which aims at solving the above problem, will be described below with reference to FIG. 7B. Note that the bullets on the ultrasound scanning lines represent focus points, and the numbers on the lower portion of the drawing represent a scan sequence. As is obvious from FIG. 7B, a characteristic feature of this scanning method is that an ultrasound scanning line r2 is scanned first at a short-distance focus point, an ultrasound scanning line r1 immediately preceding the ultrasound scanning line r2 is then scanned at a long-distance focus point, and scanning is performed in the order of r4, r3, r6, r5, . . . . In this manner, while the scanning beam moves forward from one set of a plurality of, two in this case, adjacent ultrasound scanning lines to another set, the beam moves backward in the transmission direction at each set. In addition, focus points are alternately switched in the short-distance region and long-distance region in each transmission, thereby obtaining the following effects.

Assume that the ultrasound scanning lines are sequentially scanned from the ultrasound scanning line r1 as in a conventional method. In this case, when an ultrasound pulse is transmitted to the ultrasound scanning line r1, microbubbles on the ultrasound scanning line r2 are affected, e.g., collapse. However, since the ultrasound scanning line r2 is scanned first, this adverse effect can be avoided. In addition, since the ultrasound scanning line r2 is scanned at a short-distance focus point, the influence of this scanning on the next ultrasound scanning line r1 is small. That is, microbubbles on the ultrasound scanning line r1 do not collapse much. As described above, this method can minimize the collapse of microbubbles on adjacent ultrasound scanning lines due to the application of ultrasound waves.

Note that if different focus points are set on the respective ultrasound scanning lines as in this case, since different sound fields are formed, echo signals on adjacent ultrasound scanning lines may be made uneven. Smoothing by, for example, averaging on adjacent ultrasound scanning line to reduce such unevenness is effective for an improvement in image quality.

Figure 8:
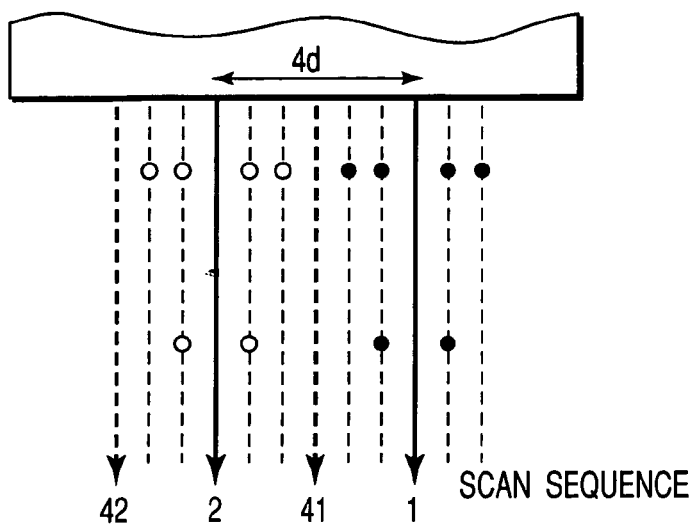
FIG. 8 is a view showing an example in which the partial scan operation in the first embodiment is applied to a linear scan.

Although the scanning method of the above embodiment is a scanning method represented by a sector probe, the present invention can also be applied to a linear type scanning method. As shown in FIG. 8, in the linear type scanning method, the intervals between ultrasound scanning lines do not depend on depth. However, the profile of the sound field formed by one beam is the same as that in the above method, and the influences on microbubbles on adjacent ultrasound scanning lines in a short-distance region still remain. When the present invention is to be applied to the linear type scanning method, ultrasound scanning lines are formed to be spaced from each other by a distance 4d, and the ultrasound scanning lines are shifted by a distance 2d to form ultrasound scanning lines spaced part from each other by the distance 4d. In this case, the time required to generate one frame becomes equal to that in the scanning method in which the transmission ultrasound scanning line density is 2d.

This embodiment presents a scanning procedure by which signals derived from microbubbles can be efficiently received, and the unevenness of contrast enhance effect within a slice can be corrected when one tomographic image is to be generated by the contrast echo method performed by administering a contrast agent. With this procedure, even if an ultrasound contrast agent exhibiting the same performance as that of a conventional contrast agent is administered, the contrast enhance effect can be relatively improved. Therefore, an improvement in blood flow diagnosis ability, especially an improvement in fine blood flow diagnosis ability, is expected.

Second Embodiment

The second embodiment provides a partial imaging method. The partial imaging method is a method of segmenting a scan plane into a plurality of local portions and scanning each local portion in an optimal scan operation sequence, instead of sequentially moving over scanning lines within the scan plane, thereby obtaining optimal (maximum) contrast on the entire scan plane and combining the resultant data into a one frame.

(Arrangement and Flow of Signals)

Figure 9:
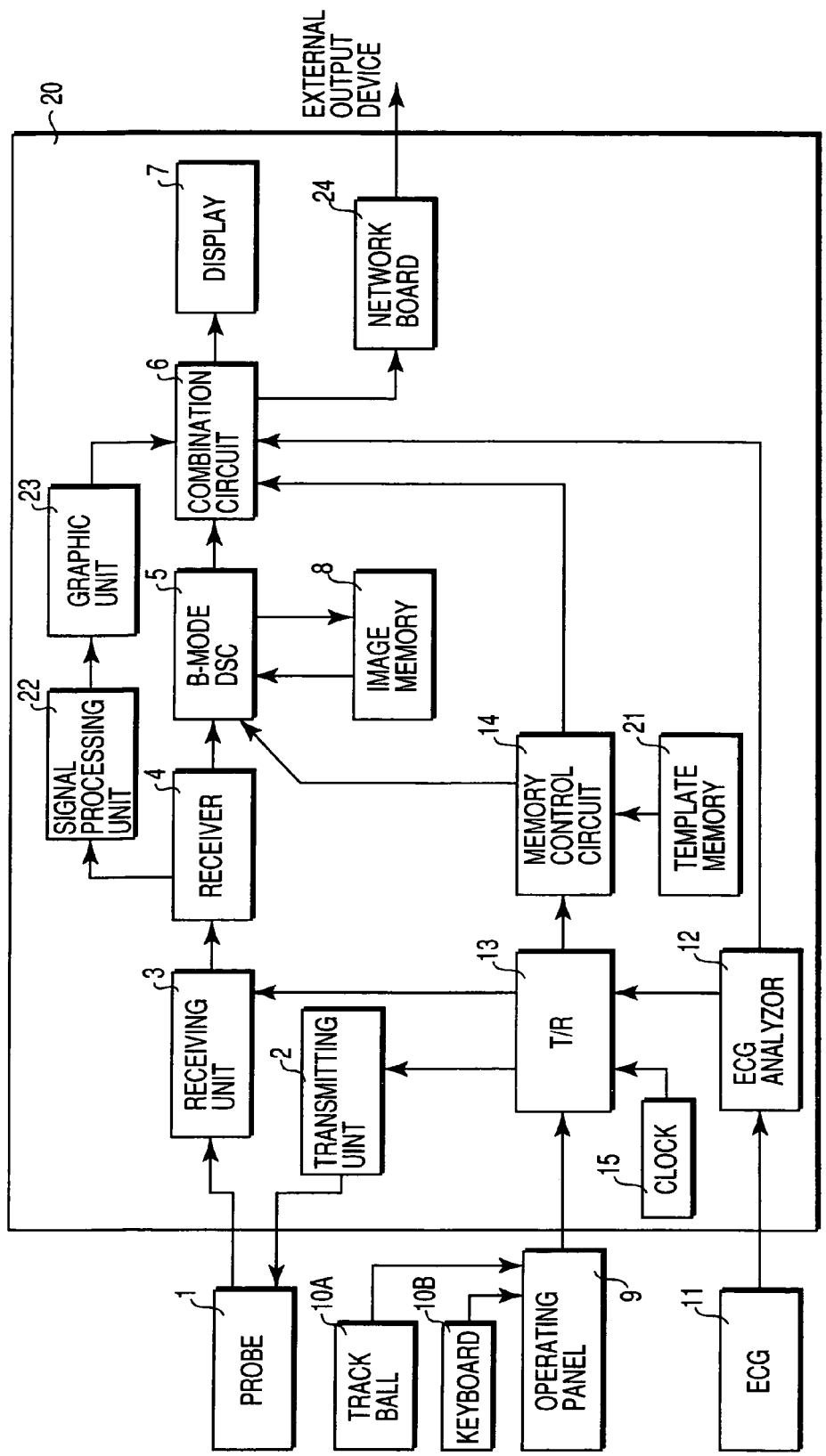
FIG. 9 is a block diagram showing the arrangement of an ultrasound diagnostic apparatus according to the second embodiment of the present invention.

FIG. 9 is a block diagram showing an ultrasound diagnosis apparatus of this embodiment. The same reference numerals as in the first embodiment denote the same parts in the first embodiment, and a detailed description thereof will be omitted. A template memory 21 stores pieces of information about a plurality of models for segmenting a scan slice into a plurality of local regions (partial regions). One optimal pattern for a sliceal shape of a portion to be diagnosed is read out from the template memory 21 in accordance with an instruction input by the operator on an operating panel 9. This template is sent to a memory control circuit 14 first, and then displayed on a display 7 in a form in which the template is superimposed on an ultrasound diagnosis image. A signal processing unit 22 performs numeric operation such as averaging echo signals from a local region or obtaining a representative value.

A graphic unit 23 performs graphic signal processing, e.g., synthesizing an image on the basis of data sent from the signal processing unit 22 and coloring a simplified graphic pattern. The image data created by this processing is output to the display 7 through a combination circuit 6. This data is also transferred to an external computer, printer, or the like through a network board 24.

(Region Segmentation in Partial Imaging Method)

This partial imaging method is roughly constituted by three steps, i.e., (a) the step of setting a diagnosis region of interest and a local region of interest, (b) the scanning step, and (c) the display step.

(a) Setting Diagnosis Region of Interest and Local Region of Interest

Figure 10A:
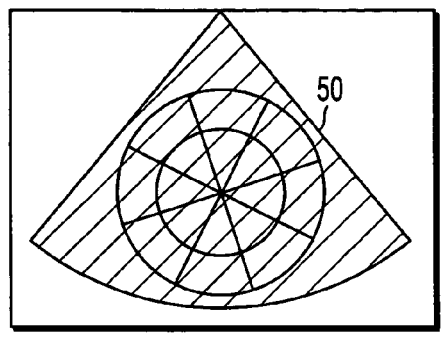
FIGS. 10A, 10B, 10C, and 10D are views showing an example of local region segmentation in the second embodiment.
Figure 10B:
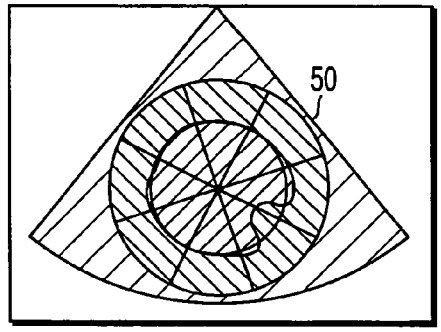

First of all, it is important to set a specific local portion toward which the diagnostic apparatus is to perform optimal scanning. The settings vary depending on an organ to be diagnosed and its slice. For example, the cardiac muscle in a cardiac minor axis image has an almost circular shape. A circular template 50 representing a local region like the one shown in FIG. 10A is selected in advance. The size of the template 50 is then adjusted by using the zoom function of the operating panel 9 or the like to almost overlap the outer ring of the template 50 on the minor axis image, as shown in FIG. 10B. If the size of a template is fixed in accordance with a routine, the template need not be displayed in some case.

Figure 10C:
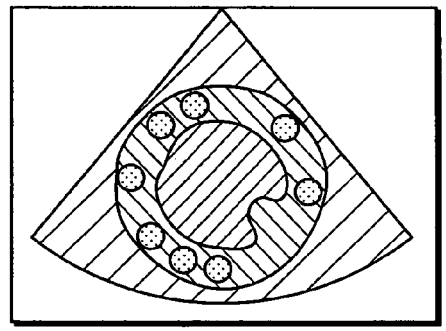
Figure 10D:
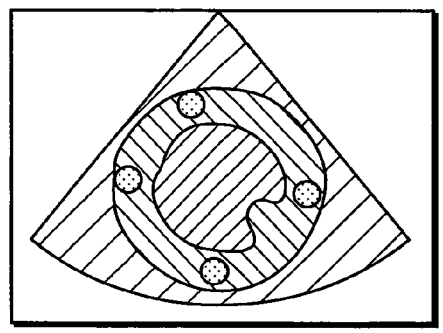

As shown in FIG. 10C, the operator then designates desired local regions with points or regions. Obviously, a plurality of regions can be designated. In this case, regions can be set at uneven intervals along the cardiac muscle. As shown in FIG. 10D, the operator designates representative points of those set above. With this operation, the apparatus performs automatic segmentation. In this example, diametrically located four points are designated to obtain a segmented region like the one shown in FIG. 10B. Obviously, the size of a template, the number of local regions segmented, and the like can be changed.

Figure 11:
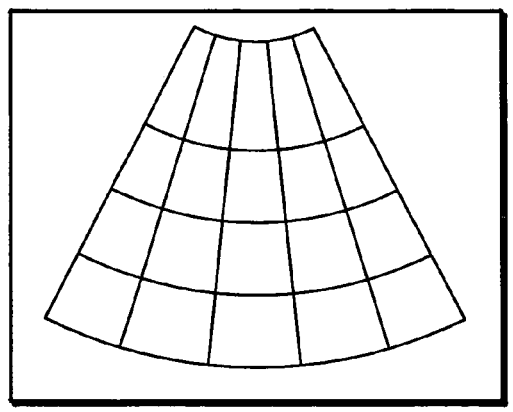
FIG. 11 is a view showing another example of local region segmentation.

In the above case, the cardiac minor axis image is exemplified. However, a template suited for the shape or the like of another slice, such as a 2-cavity cross section or major axis image, may be selectively used. In addition, the setting method shown in FIGS. 10C and 10D can also be used. In diagnosing the liver, since the liver is included in an overall slice, relatively simple local region segmentation like the one shown in FIG. 11 can be performed.

(b) Scan Operation

Figure 12:
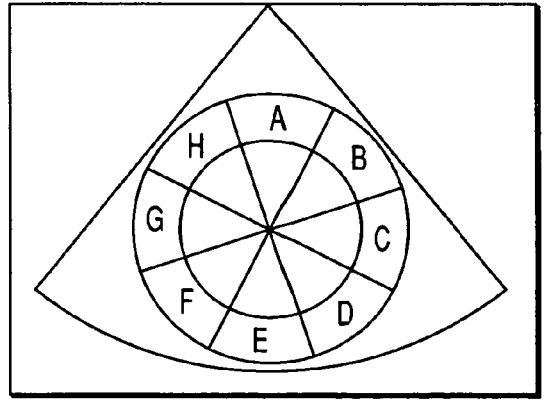
FIG. 12 is a view showing another example of local region segmentation.

The set local regions are sequentially scanned. In general, this scanning is started when the operator presses a start button on the operating panel 9. In the case shown in FIG. 12, for example, when a local region A is to be irradiated, a focus point is set at the central portion of the region A. A transmission/reception control circuit 13 changes the ultrasound transmission conditions in accordance with the position of each local position (transmission focus point) so as to almost equalize the degrees of dynamic influences on the respective local regions, i.e., sound pressures on the respective local regions and the degrees of collapse of microbubbles in the respective local regions. Typical transmission conditions that can be adjusted include the driving voltage for each transducer, the aperture width (the number of transducers to be simultaneously driven), the driving frequency, and the scanning line density.

In this case, the respective parameters are changed to almost equalize the degrees of collapse of microbubbles in consideration of biological damping (mainly determined by the transmission distance of ultrasound waves) and the irradiation angle with respect to each transducer. When the parameters associated with the driving voltage for each transducer and the number of transducers to be simultaneously driven are changed, the degrees of collapse of microbubbles can be made almost uniform by almost equalizing the sound pressures at the positions of the respective focus points. More specifically, when the driving voltage for each transducer is to be changed, the driving voltage is lowered if the focus point is located near, and vice versa. When the number of transducers to be driven is to be changed, the number of transducers to be driven is decreased if the focus point is located near, and vice versa. When the frequency is to be changed, the frequency is increased if the focus point is located near, and vice versa. Note that only one of the above parameters may be changed or a plurality of parameters may be simultaneously changed.

Strictly speaking, the value of damping varies among objects to be examined. However, a rough value can be presented to the operator on the basis of data obtained in advance by measurement. With reference to a region E exhibiting the maximum damping, relative transmission sound pressures for the respective regions are set such that $-1.5$ dB is set for regions D and F; $-2$ dB, for regions C and G, $-4.5$ dB, for shallow regions B and H, and $-6$ dB, for a shallowest region A.

If an effective echo signal is to be obtained by irradiating the local region E with ultrasound waves, the region A on the same ultrasound scanning lines is affected by the collapse of microbubbles. It is therefore useless to scan the region A immediately after the region E. This problem can be effectively solved by using an intermittent transmission method.

Figure 13:
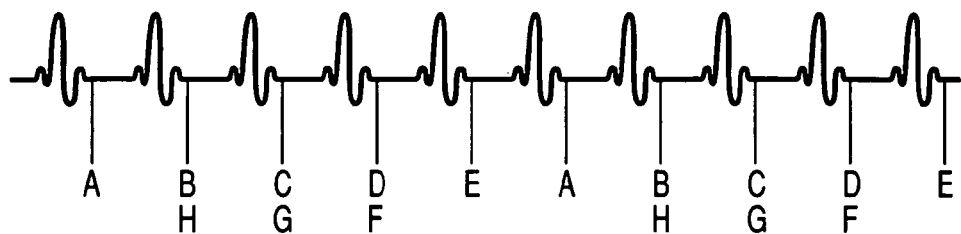
FIG. 13 is a view showing a scan operation sequence for local regions in the second embodiment.

As shown in FIG. 13, for a circulatory organ region, transmission is performed once for every heartbeat or for a few heartbeats by using triggers synchronous with an electrocardiogram. In the interval between triggers, no transmission is performed, and hence new microbubbles flow into a region of interest upon collapse of microbubbles. This makes it possible to acquire a sufficient contrast enhance effect again.

In the case shown in FIG. 13, at the same trigger timing, echo signals are generated from the pairs of local regions B and H, C and G, and D and F at the same heartbeat timing by using the parallel signal processing method. This is because each pair of regions are located at the same depth and same focal length, and do not affect each other, i.e., do not collapse microbubbles each other, since they are spaced apart from each other. In addition, in the case shown in FIG. 13, scanning from the region A to the region H is repeated a plurality of number of times.

Figure 14A:
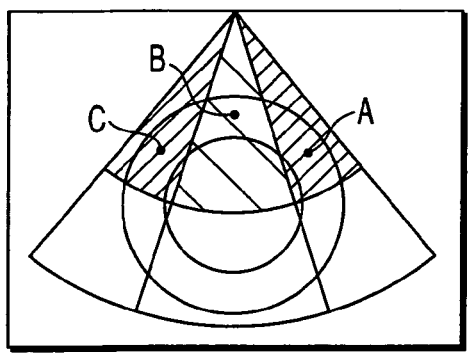
FIGS. 14A and 14B are views showing scan operation for local regions using a parallel signal processing method in the second embodiment.
Figure 14B:
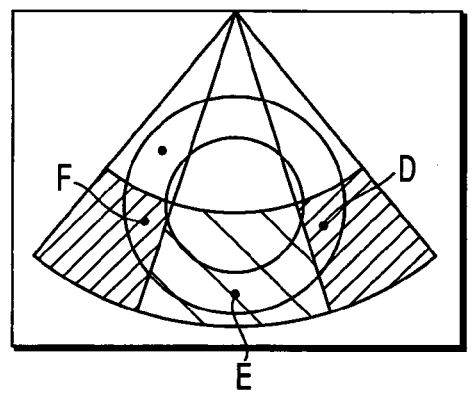

FIGS. 14A and 14B show another operation procedure. Assume that scanning is started from the right end of the screen. In this case, at the first trigger, as shown in FIG. 14A, the local regions A, B and C are simultaneously scanned by using 3-direction parallel signal processing. In each region, however, the focal length and output sound pressure can be changed, and the changed values are set as optimal values in each region. At the second trigger, as shown in FIG. 14B, similar scanning is performed for regions on which the ultrasound scanning lines at the first trigger overlap. In this method, the segmentation forms of local regions are not uniform unlike those in FIG. 11. A merit of the method is that microbubble echoes can be obtained relatively effectively with a smaller number of times of transmission/reception.

Figure 15:
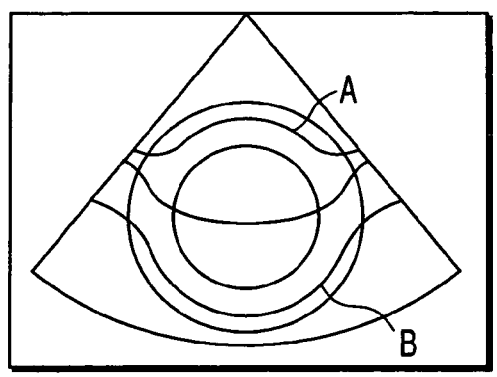
FIG. 15 is a view showing changes in focal length with movement of a transmission beam.

FIG. 15 shows an advanced method. At the first trigger, the focal length changes for each ultrasound scanning line (an illustration of ultrasound scanning lines is omitted), as indicated by "A" in FIG. 15. The output sound pressure is also controlled in accordance with a change in focal length such that output pressures on other ultrasound scanning line in this focus point portion are made uniform. At the second trigger, the focal length changes for each ultrasound scanning line as indicated by "B" in FIG. 15. As a result, at the second trigger, good echoes can be received from the entire circumferential portion of the cardiac muscle, and echoes can be acquired under a uniform sound pressure intensity along the circumferential portion of the cardiac muscle.

Figure 16:
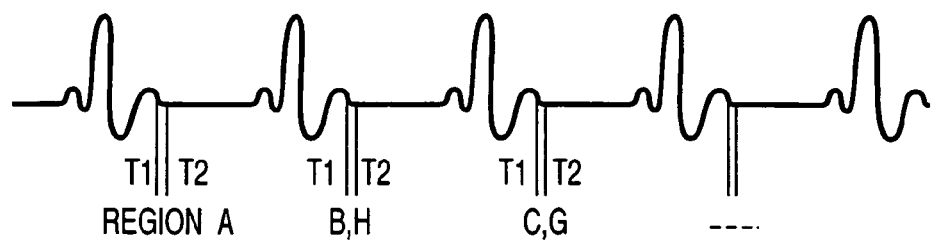
FIG. 16 is a view showing an ultrasound wave application procedure using a multishot method in the second embodiment.

The following technique can also be used to extract clearer microbubble echoes. According to this technique, as shown in FIG. 16, immediately after an echo signal is obtained by performing a scan T1 for a given region, a similar scan T2 is performed for the same region at the above trigger timing. If the scan T2 is performed at this timing, microbubbles collapse by the immediately preceding scan T1, and only an echo signal representing a tissue remains in the echoes obtained by the immediately succeeding san T2. If the receiver calculates the difference between the echo signals obtained by these two scans, only the signal derived from the collapsed microbubbles is extracted as a difference signal. As a consequence, the echoes derived from the contrast agent which are free from the influences of luminance of the living tissue can be visualized (this method will be referred to as a subtraction method hereinafter).

(c) Display

According to the data acquisition method of the present invention described above, since data (signal intensity) presenting a contrast enhance effect on the entire region of interest can be obtained by executing at least two scan procedures, the technique of combining the data and displaying the resultant image is used. In the case shown in FIG. 12 or 14, since the boundaries between the respective local regions are clear, a simple image (simple signal intensity distribution) is reconstructed by the combination circuit 6 using only data from a corresponding region, and the image is displayed on the display 7.

Figure 17A:
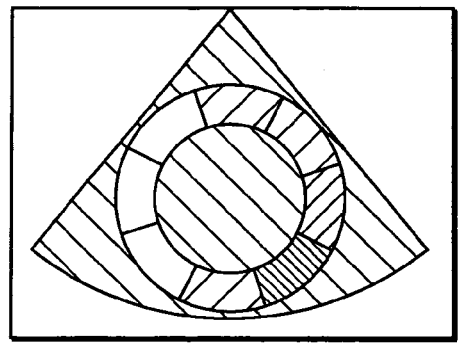
FIGS. 17A, 17B, and 17C are views showing a method of displaying local regions in the second embodiment.
Figure 17B:
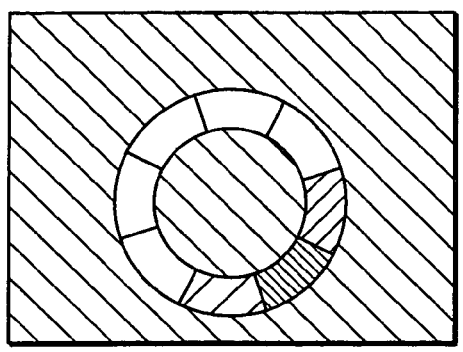
Figure 17C:
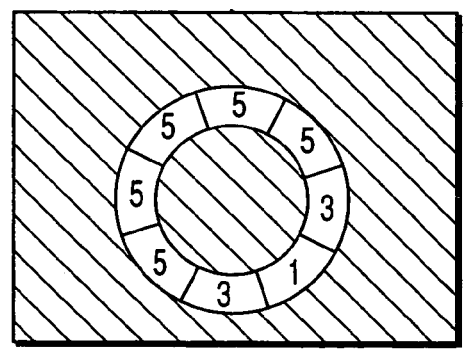

This image combining and displaying method can be applied as follows. In diagnosing a myocardial blood flow, attention is often paid to find an ischemic region of the cardiac muscle. In this case, the operator need only know fine blood flow perfusion due to a contrast agent without paying any attention to the fine form of speckle pattern of the cardiac muscle (as in the case of a scintigram in nuclear medicine). To meet such needs in diagnosis, for example, a display method of calculating the average contrast degree of each local region and displaying the calculated value as the representative value of each local region is used. Painting each region by using color information based on a color bar or the like makes the displayed information easier to discern (FIG. 17A). Alternatively, simplified display may be performed as shown in FIG. 17B. Furthermore, as shown in FIG. 17C, blood flow rates may be numerically expressed and displayed. Although the luminances and numerical values in display represent relative information, such a display method allows the operator to quickly detect an ischemic region of the cardiac muscle if it exists. These images may be displayed side by side as well as being overlaid on an original diagnostic image. More simplified display images can be added to a patient's chart or electronic patient's chart through a means such as a network as well as being output from a printer.

Third Embodiment

FIG. 18 shows the arrangement of the third embodiment. A transmission/reception control circuit 13 controls the timing of pulses from a transmitting unit. This embodiment performs intermittent transmission using a timing signal from an ECG analyzer 12 or clock 15 in accordance with a mode switching instruction sent from an operating panel 9. Intermittent transmission is transmission in which frame generation intervals are sufficiently larger than those in normal continuous transmission (20 to 100 frames/sec). For example, time intervals corresponding to four or five heartbeats are input.

Figure 19:
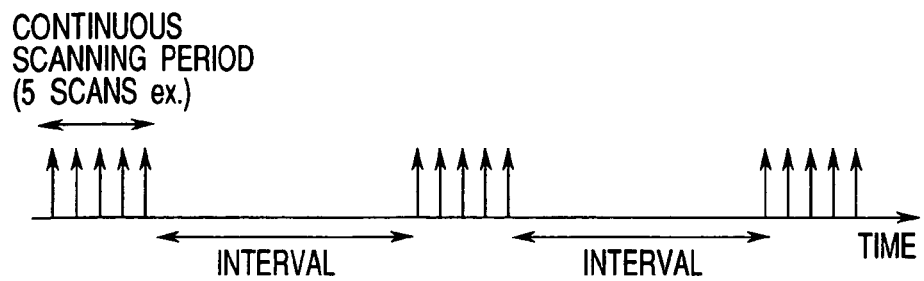
FIG. 19 is a view showing a scanning procedure in the third embodiment.

The transmission/reception control circuit 13 instructs a transmitting unit 2 to perform transmission of a plurality of frames per trigger (in other words, continuous scanning in a short period of time). FIG. 19 shows a conceptual rendering of this transmission. Referring to FIG. 19, five frames are continuously transmitted/received at predetermined time intervals (sufficiently longer than the frame rate). An image processing unit 31 combines a plurality of frames obtained per trigger by the above method and sends the resultant images to the combination circuit, and the images are displayed on the display. Prior to a description of an image processing method, diagnostic images expected from the transmission method in FIG. 19 will be described.

<Problems to Be Solved>

If the contrast agent concentration is relatively low or a contrast agent is made of microbubbles that easily collapse, most microbubbles on a slice collapse by a transmission pulse in the first frame. In the second and subsequent frames, therefore, diagnostic images are formed without any microbubbles, i.e., made of only tissue echoes.

It is, however, empirically known that there are cases other the above case. If, for example, the contrast agent concentration is high or a recently developed contrast agent containing microbubbles that are relatively resistant to ultrasounds is used, the following phenomenon occurs.

Figure 20A:
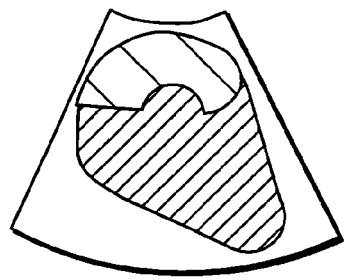
FIGS. 20A, 20B, 20C, 20D, and 20E are views showing an example of a combined image of luminance portions according to the third embodiment.
Figure 20B:
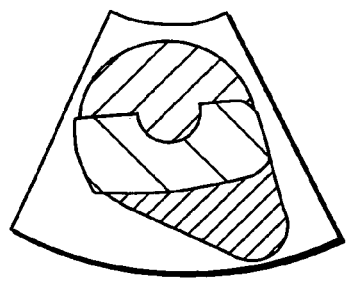
Figure 20C:
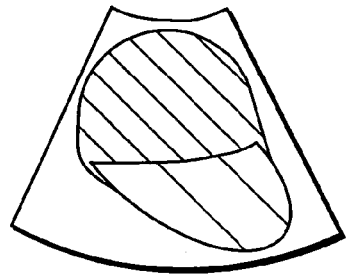
Figure 20D:
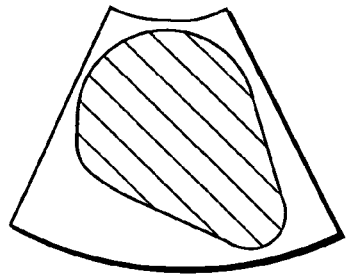
Figure 20E:
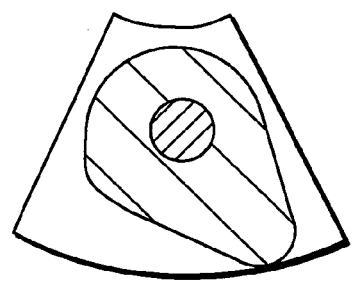

As in FIG. 20A, in transmission of the first frame (A), a contrast enhance effect is seen at a relatively short-distant portion. However, the collapsing effect of high-concentration microbubbles at the short-distance portion increases, and hence ultrasound pulses can hardly propagate to a deeper portion. As a consequence, no image is seen at a portion deeper than the short-distance portion, and the portion becomes dark. In some case, such a portion becomes darker after administration of the contrast agent than before (called shadowing). AS shown in FIG. 20B, in the second frame (B), since the microbubbles at the short-distance portion have collapsed, the contrast enhance effect decreases. However, since damping of sound waves due to microbubbles is reduced, a relatively deep portion is irradiated with a relatively high sound pressure. The contrast enhance effect at this portion increases. Subsequently, a similar phenomenon is transferred to deeper portions. When microbubbles collapse in all regions as shown in FIG. 20C, the displayed image is formed by tissue echoes (FIGS. 20D and 20E).

If this phenomenon is seen with a moving picture, the movement of the luminance based on contrast from a shallow portion to a deep portion like a curtain that drops is recognized. This phenomenon will be referred to as a "curtain phenomenon" hereinafter.

Obviously, when the above phenomenon occurs, the operator cannot examine a contrast enhance effect on an entire slice by only seeing one of a plurality of images. All the images must be joined to each other.

<Arithmetic Image Processing>

The image processing unit 31 described above performs optimal image combining processing when the above curtain phenomenon occurs. More specifically, images obtained at one trigger timing are stored in the image memory 8. The luminance signals of these images at the same coordinates in the respective frames are compared with each other to detect maximum values. Arithmetic processing for determining a luminance I(x, y) at coordinates (x, y) is given by $$I(x,y)=\text{MAX}(I_i(x,y)), I=1 \ldots N$$

where $I_i(x, y)$ is the luminance at the coordinates (x, y) in the ith frame, and N is the number of images to be compared with each other.

As a result of this processing, images like those shown in FIGS. 20A, 20B, 20C, 20D, and 20E having high-luminance contrast portions joined together are combined, and the combined image is displayed on the display. As is obvious from the result, since this image displays the luminance corresponding to the highest contrast among all the regions, the operator can examine the overall contrast degree with this one diagnostic image.

Note that this technique is similar to an MIP (Maximum Intensity Projection) method used to project three-dimensional space information on a two-dimensional plane. However, the general MIP method is used for spatial points, whereas the technique of the present invention is used for temporal points.

Note that the above arithmetic processing is relatively simple, and a combined image is preferably displayed almost in real time immediately after transmission at the trigger timing.

As described above, this embodiment cannot exhibit a sufficient effect when no curtain phenomenon occurs, but has no adverse effect. Therefore, this technique is not used in any specified condition.

<Examples of Display>

FIGS. 21A and 21B show examples of a display form. FIG. 21A shows a method based on two-window display. While intermittent transmission is observed in real time on one window, the above combined image is sequentially displayed on the other window. Referring to FIG. 21B, images obtained at one trigger timing are displayed side by side, and a combined image is simultaneously displayed. Note that all image need not have the same size. In general, since a combined image is most important for diagnosis, the image is preferably displayed in a relatively large size, as shown in FIG. 20B.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnostic apparatus for obtaining an ultrasound image of a subject into which an ultrasound contrast agent mainly composed of microbubbles is injected, comprising:
    a probe configured to transmit/receive an ultrasound wave to/from the subject;
    a transmission circuit configured to transmit an ultrasound wave to form a period during which a contrast agent flows into the object and a period during which microbubbles are collapsed by an ultrasound wave and driving said probe to perform ultrasound transmission so as to obtain ultrasound echo data corresponding to a plurality of frames in the microbubble collapse period; and
    an image generating unit configured to generate images of the plurality of frames on the basis of ultrasound echo signals received by said probe and a combined image by combining the plural images,
    wherein said image generating unit is configured to generate said combined image by comparing the images of the plurality of frames with each other and setting a luminance I(x, y) of the combined image according the relationship I(x, y)=MAX (I$_i$(x, y)), I=1 to N where MAX (I$_i$(x, y)) is a maximum luminance value of the images of the plurality of frames at coordinates (x, y), I$_i$(x, y) is a luminance at coordinates (x, y) in an ith frame of the plurality of frames, and N is a number of images of the plurality of frames to be compared with each other.

2. An apparatus according to claim 1, further comprising a display unit for displaying the combined image in real time, together with the image of each frame.

3. A scanning method for an ultrasound diagnostic apparatus for obtaining an ultrasound image of a subject into which an ultrasound contrast medium mainly composed of microbubbles is injected, comprising the steps of:

transmitting/receiving an ultrasound wave to form a period during which a contrast medium flows into the object and a period during which microbubbles are collapsed by an ultrasound wave, and performing the ultrasound transmission/reception corresponding to a plurality of frames in the microbubble collapse period; and generating images of the plurality of frames on the basis of ultrasound echo signals obtained by the transmission/reception, and generating a combined image by combining the respective images, wherein said image generating step comprises generating said combined image by comparing the images of the plurality of frames with each other and setting a luminance $I(x, y)$ of the combined image according the relationship $I(x, y) = MAX (I_i(x, y))$, $I=1$ to $N$ where $MAX (I_i(x, y))$ is a maximum luminance value of the images of the plurality of frames at coordinates $(x, y)$, $I_i(x, y)$ is a luminance at coordinates $(x, y)$ in an ith frame of the plurality of frames, and $N$ is a number of images of the plurality of frames to be compared with each other.

* * * * *